United States Patent
Bruss et al.

(10) Patent No.: US 6,727,402 B1
(45) Date of Patent: Apr. 27, 2004

(54) FILM PLASTER USING SUPPORT FILMS WITH IMPROVED SLIDING PROPERTIES AND GOOD EXTENSIBILITY, ACHIEVED BY OPTIMISING THE SURFACE STRUCTURE AND HARDNESS

(75) Inventors: Witta Bruss, Augsburg (DE); Gabriela Götz, Hamburg (DE); Robert Mayan, Buxtehude (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 10/009,922
(22) PCT Filed: May 19, 2000
(86) PCT No.: PCT/EP00/04530
§ 371 (c)(1),
(2), (4) Date: Apr. 12, 2002
(87) PCT Pub. No.: WO00/74617
PCT Pub. Date: Dec. 14, 2000

(30) Foreign Application Priority Data

Jun. 8, 1999 (DE) .......................................... 199 25 973

(51) Int. Cl.⁷ ................................................. A61F 13/00
(52) U.S. Cl. ............................... 602/43; 602/41; 602/42
(58) Field of Search ............................... 602/41–48, 52, 602/54–58

(56) References Cited

U.S. PATENT DOCUMENTS

| 3,484,835 | A |   | 12/1969 | Trounstine et al. ......... 161/130 |
| 4,318,408 | A | * | 3/1982  | Korpman |
| 4,439,391 | A |   | 3/1984  | Hung .......................... 264/317 |
| 4,518,643 | A |   | 5/1985  | Francis ....................... 428/131 |
| 5,012,801 | A |   | 5/1991  | Feret .......................... 128/155 |
| 5,143,679 | A | * | 9/1992  | Weber et al. |
| 5,147,338 | A | * | 9/1992  | Lang et al. |
| 5,328,450 | A |   | 7/1994  | Smith et al. .................. 602/59 |
| 5,445,604 | A | * | 8/1995  | Lang |
| 5,643,187 | A |   | 7/1997  | Naestoft et al. .............. 602/43 |

FOREIGN PATENT DOCUMENTS

EP          446 431          9/1991  ........... A61F/13/02

* cited by examiner

Primary Examiner—Nicholas D. Lucchesi
Assistant Examiner—Lalita M. Hamilton
(74) Attorney, Agent, or Firm—Norris McLaughlin & Marcus

(57) ABSTRACT

A film plaster, especially for covering wounds and preventing or treating blisters, which comprises a two-layer elastic film, the upper layer being harder and thinner than the lower layer, and being structured, and the surface of the lower layer being coated, where appropriate, with a pressure-sensitive adhesive composition.

11 Claims, 2 Drawing Sheets

Figure 1:
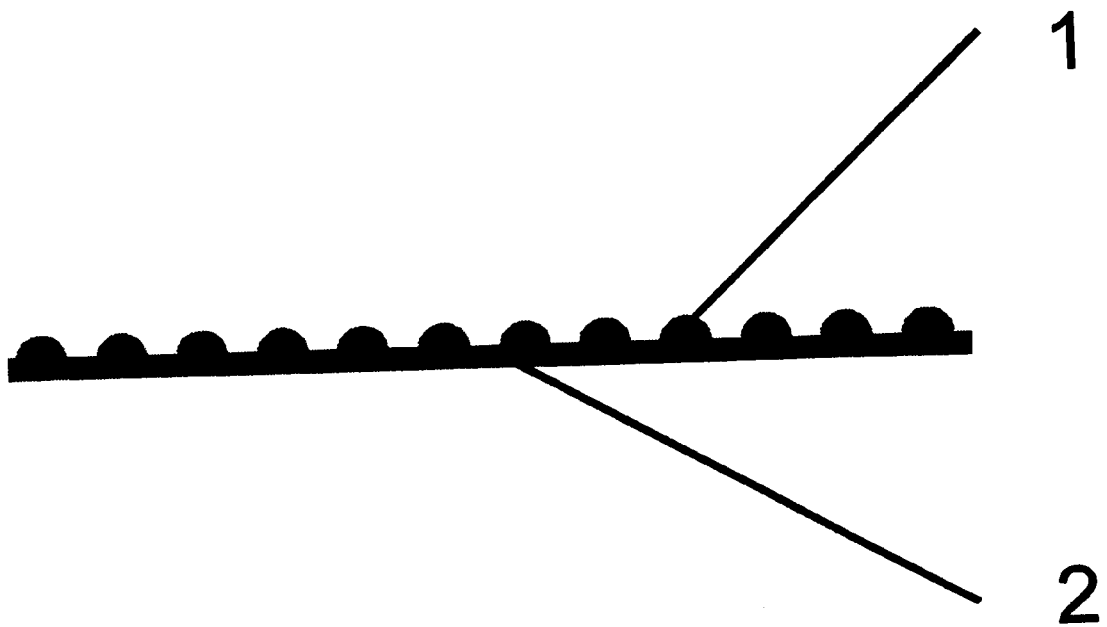

FILM PLASTER USING SUPPORT FILMS WITH IMPROVED SLIDING PROPERTIES AND GOOD EXTENSIBILITY, ACHIEVED BY OPTIMISING THE SURFACE STRUCTURE AND HARDNESS

This is a 371 of PCT/EP00/04530 filed May 19, 2000 (international filing date).

The invention relates to film plasters, especially for covering wounds and preventing or treating blisters, using backing films having defined surface properties.

BACKGROUND OF THE INVENTION

Films find frequent use in plasters and first aid dressings on account of their imperviousness to water and to microbes, their conformability, and their high level of compatibility.

Accordingly, DE 43 14 834 A1 discloses a film-based dressing material covered on one side with a backing material whose size is the same as that of the film and which has at least one grip strip, and on the other side is provided with a self-adhesive layer. Essential to the invention here is that the grip strips are disposed within the peripheral boundary of the backing material. There is preferably only one grip strip on the backing material. A plaster of this kind with a polyurethane film is available commercially under the name "Aqua Protect"® from Beiersdorf.

DE 40 26 755 A1 discloses a film-based dressing material covered on one side with a support material whose size is the same as that of the film and which has at least one grip strip, and on the other side is provided with a self-adhesive layer. In contrast to the dressing material of DE 43 14 834 C2 the grip strips for removing the backing material are disposed within the peripheral boundary of the backing material. Here too, there is preferably only one grip strip on the backing material. This plaster with a polyurethane film is available commercially under the name "Cutifilm"®, again from Beiersdorf.

Medical plasters, wound dressings, dressings, and fixings of all kinds are often subject to a phenomenon that leads to premature, unintended detachment. This phenomenon is turnup, where the product rolls back starting usually from one corner or else one edge of the plaster.

Once the plaster has come away at one point, there follows a chain reaction which leads very rapidly to complete detachment. With particular frequency, this turnup occurs with plasters worn under clothing or inside footwear. The reason is the rubbing (friction) of the clothes or shoe on the surface of the plaster. This frictional force gives rise to a dynamic shear load on the pressure-sensitive adhesive composition, which usually leads very rapidly to breaking of the bond in the edge region. After the adhesive composition has been released at one edge, the textile or leather clings to the projecting composition and, as a result of the tangentially bearing force, causes turnup and further, accelerated detachment of the whole plaster.

One way of preventing premature detachment is to increase the adhesion of the pressure-sensitive adhesive composition to the skin. This tackiness cannot, however, be increased ad infinitum, since otherwise there may be skin irritation, pain, and disturbance of the wound in the course of the intended detachment of the product.

From EP 0 409 587 A1 it is known to what extent the premature detachment of plasters is affected by the contact area A of the backing film, i.e., the area over which two sliding bodies are actually in contact.

It describes the use of thermoplastic films which during or after the extrusion in the melted state are embossed by an embossing roller. Best results are obtained with a structure in which the contact area represents approximately 25% of the total area.

Using this process, different surfaces can be produced only by employing different embossing rollers. This requires the corresponding rollers first to be produced, in complex and costly processes. A further disadvantage of the process is the generation of positive/negative structures on both sides of the backing. This structure imposes exacting demands in the context of the partial coating with adhesive composition and the placing and anchoring of wound contact materials. The production of multilayer films from hard and soft starting materials is not described. The use of multilayer films to form plasters produced by coating polymer dispersions or polymer solutions onto embossed papers or films is not a subject of the disclosure.

SUMMARY OF THE INVENTION

EP 0 446 431 outlines how using casting papers comprising polymer solutions it is possible to produce backing materials for medical use. Subject matter of this invention is, however, a laminate comprising polymeric film layers and a macroporous textile material. The casting paper used in accordance with one example is not described in more detail. Nor is there any indication of the improvement of slip properties by optimizing the contact area and the elasticity of the outer layer, achieved by using casting papers having a structured surface and starting materials of different hardness.

DETAILED DESCRIPTION

U.S. Pat. No. 5,643,187 describes a film plaster whose backing film consists of two layers, the outer layer of the film being relatively hard, thin, and slippery and the inner layer being relatively soft and thick. Through this combination of two different materials, a film backing having improved slip properties and adequate stability is said to be obtained. This document outlines exclusively the use of film backings having smooth, unstructured surfaces. The improvement of slip properties by optimizing the contact area is not a subject of the description.

A disadvantage of this method of improving the slip is an unavoidable reduction in stretchability, elasticity, and hence conformability of the backing film. Considerably greater force must be applied in order to stretch hard films or film layers, so that in a plaster application there may be instances of skin irritation and a delayed healing process owing to mechanical loading of the wound.

From DE 197 06 380 it is known that a film having direction-dependent water vapor permeability may be produced by multilayer construction. Coextrusion of thermoplastic polyurethanes having different water vapor permeabilities gives a multilayer film which in turn exhibits different permeabilities to water vapor, depending on which side of the film is facing the moisture source. The invention likewise describes the use of polyurethane layers which may differ not only in water vapor permeability but also in their hardness; optimizing slip properties by varying the contact area of the films, however, is not described.

WO 98/41590 describes the production of films based on polystyrene block copolymer/polystyrene blends by melt extrusion, said films featuring good severability and being simple to make available from a dispenser pack. Production and properties, especially slip properties and stretch properties, of films comprising two or more layers of different hardness are not a subject of the overall disclosure.

According to the first law of friction, the frictional force $F_f$ is equal to the product of friction coefficient $\mu$ and normal force $F_n$. This coefficient is a measure of the force that must be used to move a body on a surface, $\mu_s$ denoting the static and $\mu_k$ the kinetic (sliding) friction coefficient.

The development of backings having good slip properties, i.e., low friction coefficients, is therefore a central starting point for preventing the turnup effect outlined above. Although to date, as set out in particular by Ludema (Ludema, K. C., Friction, Wear, Lubrication: a Textbook in Tribology, CRC Press, Boca Raton 1996), neither exact nor approximate methods exist for deriving friction or wear properties from fundamental principles, an inspection of the literature permits conclusions to be drawn about parameters which determine the size of $\mu_s$ and $\mu_k$.

Static friction is governed (Blau, P J.; Friction Science and Technology, Marcel Dekker, New York 1996) by the following expression:

$$\mu_s = (\tau_m/P^*)A$$

where $\tau_m$ is the shear strength,

A is the contact area, and

P* is the combination of normal force and adhesion.

Sliding friction between two bodies is determined by a range of interacting effects (Bhushan, B., Gupta, B. K.; Handbook of Tribology, McGraw-Hill New York 1991). Besides adhesion components, there occur plowing effects, roughness effects, deformation effects, and, particularly in the case of viscoelastic materials, damping effects. The relative contribution of these effects depends on the materials involved, the surface topography, the state of the sliding surfaces, and the ambient conditions.

Investigations by Bartenev (Bartenev, G. M., Lavrentev, V. V.; Friction and Wear of Polymers, Elsevier Amsterdam 1981) and Rabinowicz (Rabinowicz, E.; Friction and Wear of Materials, Wiley-Interscience, New York 1995) reveal the friction coefficient $\mu_k$ to be determined not only by contact area but also by parameters such as roughness, hardness, elasticity modulus, and surface energy of the materials.

The hardness of a plastic is generally stated as the Shore hardness. In the testing of elastomers and rubber, in accordance with DIN 53505 1987-06, the Shore hardness corresponds to the resistance to the penetration of a frustum (A or C) or, respectively, of a rounded cone (D) which is measured by the compression of a spring having a defined spring characteristic and is expressed in dimensionless Shore A (C, D) hardness units. For the testing of steel, the Shore rebound hardness is measured in what is known as a scleroscope, which determines the rebound height of a hammer that falls on the test area in a vertical tube. This is more an elasticity test, and for that reason the measurements are of only limited comparability with those from a Brinell or Vickers hardness test (Römpp Lexikon Chemie—Version 1.5, Stuttgart/New York: Georg Thieme Verlag 1998). As may be derived from the above equations, there is a direct correlation between the hardness and slip of a material.

For the conformability and wear comfort of a film plaster, in contrast, the softness, stretchability, and elasticity of the backing film are of central importance. If excessive forces are needed to stretch the backing material while being worn on the skin, caused by body movements such as flexing of limbs or tautening of muscles, these high forces lead to a feeling of tightness and of instances of skin irritation. Proven as a suitable parameter for determining the conformability of a film backing during application on the skin is the 100% modulus. This figure indicates the tensile stress needed to stretch the film by 100%, and may be determined in accordance with DIN 53 504.

It is an object of the invention to avoid the disadvantages known from the prior art and to provide a film plaster which is self-adhesive on one side, possesses good elasticity and stretchability, and owing to improved slip properties does not release unintentionally from the skin side to which it has been bonded previously.

This object is achieved by means of a film plaster as specified in the main claim. The subclaims relate to advantageous developments of the film plaster.

Accordingly, the present invention provides a film plaster, especially for covering wounds and preventing or treating blisters, which comprises a two-layer elastic film, the upper layer being harder and thinner than the lower layer, and being structured, and the surface of the lower layer being coated, where appropriate, with a pressure-sensitive adhesive composition.

In a first preferred embodiment, between the upper layer and the lower layer there is at least one further layer which serves, inter alia, to improve the imperviousness to microbes.

In accordance with the invention, the structure of the upper layer is understood to be a raised patterning, so that the layer is not constructed flatly but instead has three-dimensional elevations and depressions. Alternatively, in one preferred embodiment, the upper layer may comprise individual discrete (i.e., separate) segments.

The film plaster therefore has a three-dimensionally configured surface which is formed by the upper layer or outer layer and which in turn is thinner and harder than the lower layer and than other layers which face the adhesive composition. Surprisingly, by optimizing the structure and hardness of the outer layer, films having improved slip and good conformability and elasticity are obtained.

The surface structure of the films may be laid down in particular by the choice of casting substrate. Preferred casting substrates are those having a structure in which individual elevations are completely separated from one another by depressions. The layer construction of the film may be controlled so that only these elevations are composed of hard, slippery material. The polymer concentration in the dispersion or solution and the width of the gap during coating of the casting substrate determine the thickness of the hard outer layer.

When highly dilute solutions or dispersions, using wetting agents were appropriate, are coated using a low gap width, film embodiments are obtained in which even the elevations consist largely of soft polymer.

Further layers of the film backing of the invention are produced by applying soft, elastic, polymer types.

In the advantageous embodiment it is ensured that the hard, slippery elevations are separated from one another by soft, elastic, "valleys". These elevations provide the improved slip, while the elasticity and flexibility is ensured by the soft, flexible base material.

FIG. 1 shows a film of the invention which is composed of a hard, slippery outer layer 1. The outer layer 1 is composed of individual segments which are completely separate from one another and are applied on a soft elastic base layer 2.

Figure 2:
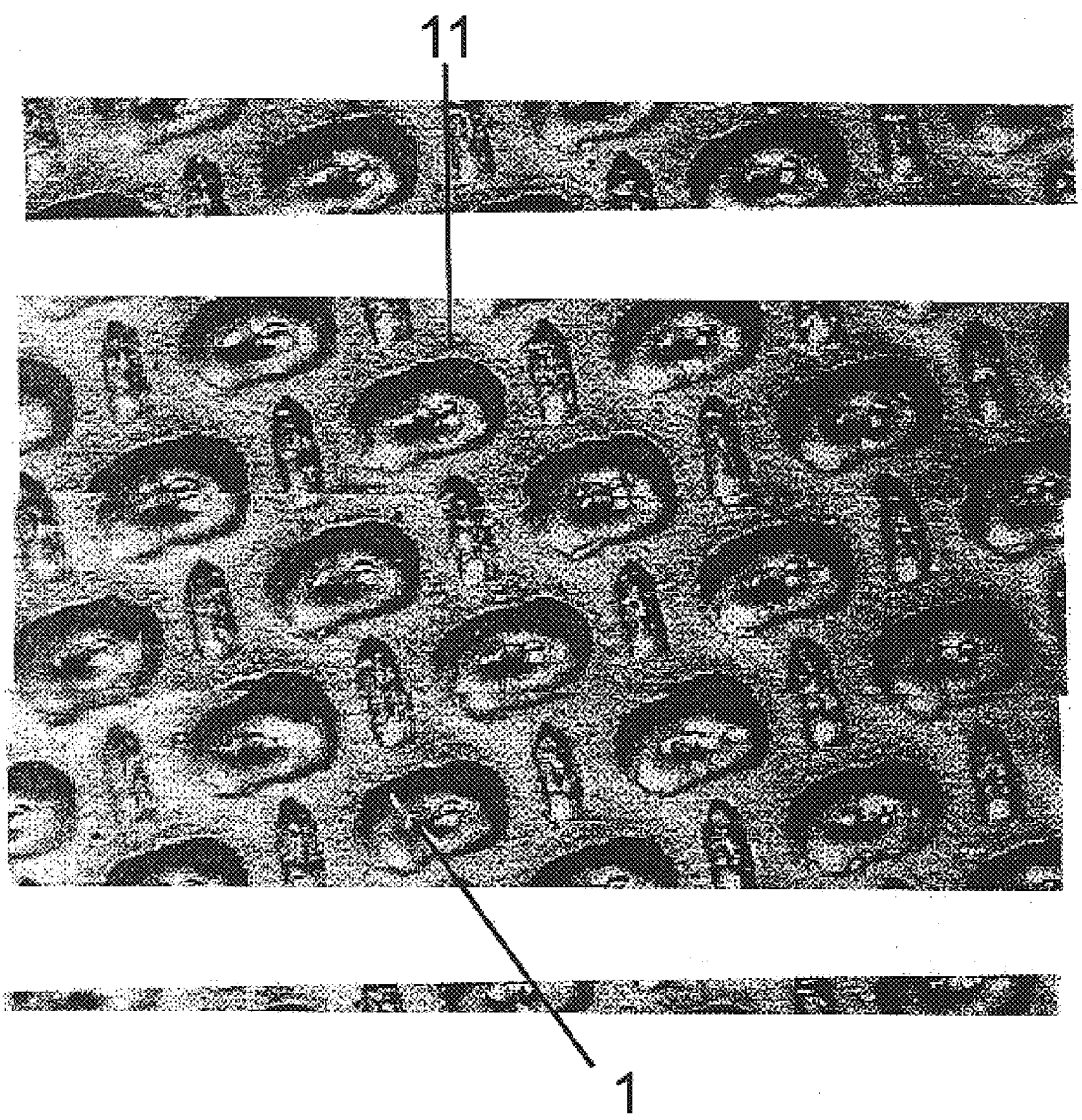

FIG. 2 shows a plan view of a film plaster of the invention. The outer layer 1 is formed of discrete segments 11 which protrude.

The casting papers or casting substrates are generally commercial, water-resistant silicone-coated or polypropylene-coated papers which are used primarily for producing synthetic leather and are available in a range of variants. Through the choice of paper it is possible to influence critically the three-dimensional form and thus the slip properties of the film. A suitable casting substrate is also any other film or paper (for example, films of polyethylene or polypropylene-coated casting papers) that has a desired surface structure and is not disintegrated or chemically destroyed by the polymer dispersions or solutions used.

Casting papers having the desired surface structure may be obtained, inter alia, from the companies Arconvert S.p.A. (Arco, Italy), Binda S.p.A. (Crusinallo/Omegna, Italy) or Ardo Wiggins Casting Papers Limited (Basingstoke, England).

An advantage of the plaster film of the invention over the prior art as documented in particular in EP 0 409 587 A1 or U.S. Pat. No. 5,643,187 is the optimum synthesis between slip and stretchability of a backing material achieved through the use of a hard, three-dimensional configured surface. When a soft film is embossed, as described in EP 0 409 587 A1, optimum slip properties are not obtained because soft materials have higher friction coefficients than hard materials. The application of a continuous, unstructured hard layer, as illustrated in U.S. Pat. No. 5,643,187, provides good slip but drastically reduces the stretchability and hence the conformability of the film backing.

Preferred dispersions for producing medical plasters for covering wounds and treating or preventing blisters are polyurethane dispersions which are available, for example, from Bayer AG, Leverkusen (DE), under the names Impranil and Impraperm. By the addition of appropriate additives, these dispersions may be foamed, so that foams as well may be produced as backing. By blending different grades of Impranil and/or Impraperm and optionally preparing multi-ply layers by successive application of different foamed or unfoamed dispersions to a paper, it is possible to produce backing materials having desired properties such as hardness, elasticity modulus, stretchability, water vapor permeability, roughness, handle, and esthetics. The films or foams, which are colorless per se, may be colored by adding commercial pigments such as Euderm (Bayer AG, Leverkusen, DE).

A preferred polyurethane film, composed exclusively of unfoamed layers, is from about 10 to 500 $\mu$m thick and transparent; a polyurethane film composed of foamed and unfoamed layers is from about 0.1 to 3 mm thick. Both variants have elongations at break of more than 450% and water vapor permeabilities of more than 500 g/m$^2$ in 24 h at 38° C. and 95% relative humidity in accordance with DAB [German Pharmacopeia].

Films of the invention may also be obtained using commercial polystyrene block copolymer compounds. Suitable compounds in a hardness range of from 29 to 96 Shore A may be acquired, for example, from Gummiwerk Kraiburg, 84464 Waldkraiburg (DE), under the designation Thermolast K, from Silac, La Rochefoucauld, France, under the designation Lacbloc (SEBS compounds), or Terlac (SBS compounds), or from Albis Plastic, Hamburg (DE), under the designation Evoprene G or Evoprene Super G. Since polystyrene block copolymers feature outstanding compatibility with other polymers, further polymers such as polystyrene, for example, may be admixed to the solutions.

In addition, however, it is also possible to use films based on polystyrene block copolymers or other known film-forming elastic polymers such as acrylates, for example.

The thickness of the films may be between about 10 to 500 $\mu$m, preferably from 15 to 80 $\mu$m, the weight, correspondingly, between about 15 to 350 g/m$^2$, preferably from 15 to 100 g/m$^2$, the ultimate tensile force in the longitudinal direction between about 2 to 100 N/cm, preferably from 5 to 40 N/cm, the 100% modulus less than 20 MPa, preferably less than 15 MPa, and the elongation at break in the longitudinal direction between about 100 to 1000%.

To the skilled worker it is immediately evident that films of the invention may also be produced by using polymer solutions instead of polymer dispersions. In that case the thickness of the outer layer and base layers may be set by way of the concentration of the polymer in the corresponding polymer solutions.

Accordingly, by the choice of substrate and the selection, preparation, and processing of the base materials, it is possible to obtain backing materials having custom tailored slip and stretch properties. To the skilled worker it is immediately evident that these parameters are also appropriate for producing films having desired esthetics and tactility. For applications where the slip properties are less prominent than the sensation, qualities such as conformability and pleasing tactility may be improved by targeted optimization of the parameters mentioned.

Pressure-sensitive adhesive (PSA) compositions used may be commercial, medical grade adhesive compositions. The PSA composition in the film preferably has a bond strength for steel of, for example, about 2 to 4 N/cm, it being necessary to reinforce the reverse of the test material for the measurement with an inelastic adhesive film, since the backing film is very stretchable. The measurement itself takes place in accordance with DAB 9.

On its self-adhesive side, which subsequently faces the skin, the film plaster of the invention is usually covered over its entire width, up until the time of use, with an antiadhesive carrier material, such as siliconized paper. This material protects the selfadhesive layer, which comprises an adhesive composition possessing good skin compatibility, based for example on acrylate and applied preferably by the transfer method, and also stabilizes the product as a whole. The cover may be designed conventionally in one piece or, preferably, as two parts.

The film plaster may be used as it is or else a customary absorbent wound contact material or another functional material having beneficial effects on the healing of wounds or blisters may be additionally applied centrally in an appropriate width, so that the plaster can be used directly as a wound dressing. A dressing of this kind with all-round bonding is especially advantageous since it is impervious to microbes and resistant to water.

For sterilization, the product may be packaged and $\beta$-irradiated by standard techniques.

The following techniques have been found particularly advantageous for the production of the film plaster.

First of all, a polyurethane dispersion is applied to an embossed, water-resistant (and, where appropriate, silicone- or polypropylene-coated) paper or embossed film so as to give a structured layer composed in particular of individual segments separate from one another. The composite is dried.

A second polyurethane dispersion is applied to the first and the composite is dried again. The resulting polyurethane film is coated with a pressure-sensitive adhesive composition, which may be provided with a wound cover and an antiadhesive carrier material, and the water-resistant silicone- or polypropylene-coated paper or the film is removed.

If desired, further layers having the desired properties are applied between the first and the second layers.

Full-area or partial coating of the smooth surface of the backing with PSA composition gives the medical plaster.

The production of the polystyrene block copolymer backing films comprises dissolving a first polystyrene block copolymer compound in an organic solvent, preferably toluene, applying the solution to an embossed polymer film, made of polyethylene, for example, or to a polypropylene-coated casting paper, so as to give a structured layer composed in particular of individual segments separate from one another, drying the composite, dissolving in an organic solvent and applying a second polystyrene block copolymer compound to the first, drying the composite, coating the resulting film with a pressure-sensitive adhesive composition, providing the pressure-sensitive adhesive composition, if desired, with a wound cover and an antiadhesive carrier material, and removing the polymer film or the casting paper.

Advantages of the production process described here in accordance with the invention, which are based not on embossing but instead on the application of dissolved or dispersed polymer compounds to substrates having a structured surface, are a high-flexibility, simple alteration of the structure of the backing by changing the substrate, low costs, and the very large number of available papers and films. Furthermore, this process produces a surface having a desired structure and a smooth opposing surface which is easy to coat with adhesive composition.

The film plaster of the invention is described below in exemplary embodiments without wishing thereby to restrict the invention in any way whatsoever.

EXAMPLE 1

Casting paper BNS Cortina (from Binda) is knife coated with an Impranil DLF dispersion thickened with 0.2% Collacral PU85 (BASF AG, Ludwigshafen (DE)) so that only the depressions of the paper are filled with dispersion.

After the outer layer has dried, second and third layers composed of Impranil DLN/DLH 1:1 thickened with 0.25% Collacral PU85 are applied.

After these layers have been dried and the casting paper has been removed, the soft, stretchable backing film with a structured, hard outer layer is obtained.

EXAMPLE 2

Casting paper BNS Cortina (from Binda) is knife coated with an Impranil DLF dispersion diluted 1:4 with water and treated with 0.3% Surfynol 504 wetting agent (Biesterfeld, Hamburg (DE)) so that only the depressions of the paper are filled with dispersion.

After the outer layer has dried, second, third, and fourth layers composed of Impranil DLN/DLH 1:1 thickened with 0.25% Collacral PU85 are applied.

After these layers have been dried and the casting paper has been removed, the soft, stretchable backing film with a structured, hard outer layer is obtained.

The table below shows slip and stretch properties of films of the invention, the friction coefficient $\mu$ having been determined in accordance with DIN 53375 and the 100% modulus in accordance with DIN 53504. The composition of the base layers is listed first, then the construction of the outer layer. The column headed "Substrate" describes the particular casting paper used. Films listed as comparative examples were produced from soft, stretchable polymer without a hard, slippery outer layer.

TABLE 1

Properties of films of the invention

| No. | Base layer | Outer layer | Substrate | 100% Modulus [MPa] | $\mu$ |
|---|---|---|---|---|---|
| Comp. Ex. 1 | DLH/DLN 1:1 | — | AW Pearl | 2.3 | 2.7 |
| 2 | DLH/DLN 1:1 | DLF/PU 85 | AW Pearl | 2.6 | 0.4 |
| 3 | DLH/DLN 1:1 | DLF/wetting agent | AW Pearl | 3.6 | 0.5 |
| Comp. Ex. 2 | DLH/DLN 1:1 | — | BNS Cortina | 1.5 | 1.8 |
| 4 | DLH/DLN 1:1 | DLF/PU 85 | BNS Cortina | 2.3 | 0.4 |
| 5 | DLH/DLN 1:1 | DLF dil./ wetting agent | BNS Cortina | 1.7 | 0.5 |

Comparison of the films with and without a hard, structured outer layer clearly shows the advantages of the backing materials of the invention. The friction coefficients p decrease drastically in the presence of the hard outer layers. The conformability and stretchability, measured as the 100% modulus, on the other hand, are largely retained. The advantages of the films of the invention are shown with particular clarity by No. 5. Here, the hard outer layer was made so thin, by dilution of the polyurethane dispersion and simultaneous addition of a wetting agent, that the 100% modulus remains virtually unchanged.

What is claimed is:

1. A film plaster for covering wounds and preventing or treating blisters, which comprises an at least two-layer elastic film having an upper layer and a lower layer, the upper layer being harder and thinner than the lower layer, and being structured, and the surface of the lower layer being optionally coated with a pressure-sensitive adhesive composition.

2. The film plaster as claimed in claim 1, wherein between the upper layer and the lower layer there is at least one further layer.

3. The film plaster as claimed in claim 1, wherein the upper layer is composed of individual, separate segments.

4. The film plaster as claimed in claim 1, wherein the layers are produced from polyurethane dispersions, polystyrene block copolymers or acrylates.

5. The film plaster as claimed in claim 1, covered over its entire width, up until the time of use, with an antiadhesive carrier material.

6. The film plaster as claimed in claim 1, comprising an absorbent wound contact material or another functional material having beneficial effects on the healing of wounds or blisters.

7. A process for producing a film plaster, which comprises applying a first polyurethane dispersion to an embossed film or to an embossed water-resistant paper so as to form a structured layer composed of individual segments separate from one another, drying the resulting composite, applying a second polyurethane dispersion to the first, said second polyurethane dispersion being formulated to form a film which is softer than a film formed by said first polyurethane dispersion, drying the resulting composite, to form a polyurethane film, coating the polyurethane film with a pressure-sensitive adhesive composition, optionally providing the pressure-sensitive adhesive composition with a wound cover and an antiadhesive carrier material, and removing the embossed film or water-resistant paper.

8. A process for producing a film plaster, which comprises dissolving a first polystyrene block copolymer compound in an organic solvent to form a solution, applying the solution to an embossed polymer film or to a polypropylene-coated casting paper, so as to form a structured layer composed of individual segments separate from one another, drying the composite, dissolving a second polystyrene block copolymer in an organic solvent to form a solution, said second polystrene block copolymer being formulated to form a film which is softer than a film formed by said first polystyrene block copolymer, and applying it to said composite to form a second composite, drying the second composite, to form a film coating the film with a pressure-sensitive adhesive composition, optionally providing the pressure-sensitive adhesive composition with a wound cover and an antiadhesive carrier material, and removing the polymer film or the casting paper.

9. The film plaster of claim 5, wherein said antiadhesive carrier material is siliconized paper.

10. The process of claim 8, wherein said organic solvent is toluene.

11. The process of claim 8, wherein said polymer film is a polyethylene film.

* * * * *

UNITED STATES PATENT AND TRADEMARK OFFICE
CERTIFICATE OF CORRECTION

PATENT NO. : 6,727,402 B1
DATED : April 27, 2004
INVENTOR(S) : Bruss et al.

It is certified that error appears in the above-identified patent and that said Letters Patent is hereby corrected as shown below:

Column 4,
Line 47, "were appropriate" should read -- where appropriate --

Column 6,
Line 49, "β-irradiated" should read -- α-irradiated --

Column 8,
Line 23, "coefficients P" should read -- coefficients $\mu$ --

Signed and Sealed this

Third Day of May, 2005

JON W. DUDAS
*Director of the United States Patent and Trademark Office*